United States Patent
Girouard et al.

(10) Patent No.: US 10,342,451 B2
(45) Date of Patent: Jul. 9, 2019

(54) METHOD AND APPARATUS FOR DETECTING SEIZURES INCLUDING LOOSE ELECTRODE MONITORING

(71) Applicant: Brain Sentinel, Inc., San Antonio, TX (US)

(72) Inventors: Michael R. Girouard, San Antonio, TX (US); Michael E. Halleck, Frederick, CO (US); Michael D. Halleck, Frederick, CO (US)

(73) Assignee: Brain Sentinel, Inc., San Antonio, TX (US)

( * ) Notice: Subject to any disclaimer, the term of this patent is extended or adjusted under 35 U.S.C. 154(b) by 469 days.

(21) Appl. No.: 15/030,349

(22) PCT Filed: Oct. 22, 2014

(86) PCT No.: PCT/US2014/061783
§ 371 (c)(1),
(2) Date: Apr. 18, 2016

(87) PCT Pub. No.: WO2015/061459
PCT Pub. Date: Apr. 30, 2015

(65) Prior Publication Data
US 2016/0242668 A1    Aug. 25, 2016

Related U.S. Application Data

(60) Provisional application No. 61/894,793, filed on Oct. 23, 2013.

(51) Int. Cl.
A61B 5/0488    (2006.01)
A61B 5/00      (2006.01)
A61B 5/0424    (2006.01)

(52) U.S. Cl.
CPC .......... *A61B 5/0488* (2013.01); *A61B 5/4094* (2013.01); *A61B 5/6843* (2013.01); *A61B 5/6844* (2013.01); *A61B 5/0424* (2013.01)

(58) Field of Classification Search
CPC .... A61B 5/0424; A61B 5/0488; A61B 5/4094
See application file for complete search history.

(56) References Cited

U.S. PATENT DOCUMENTS 4,141,351 A    2/1979  James et al.
4,577,639 A    3/1986  Simon et al.
(Continued)

FOREIGN PATENT DOCUMENTS

JP    2010538775 A    12/2010
WO    WO2009036770    3/2009

OTHER PUBLICATIONS

US 8,469,921 B2, 06/2013, Robertson et al. (withdrawn)
(Continued)

*Primary Examiner* — Sean P Dougherty
*Assistant Examiner* — Nicholas E Kolderman
(74) *Attorney, Agent, or Firm* — Pizarro Allen PC

(57) ABSTRACT

Apparatuses and methods for monitoring a patient for seizure activity and for verifying the contact integrity of electrodes included among an EMG sensor may include generating a test signal of known periodicity and applying the signal to at least one electrode in a sensor system. The test signal may be monitored to verify contact integrity of the electrodes.

23 Claims, 4 Drawing Sheets

(56) References Cited

U.S. PATENT DOCUMENTS

| | | | |
|---|---|---|---|
| 4,917,099 A | 4/1990 | Stice | |
| 5,002,064 A | 3/1991 | Allain et al. | |
| 5,197,479 A | 3/1993 | Hubelbank et al. | |
| 5,792,063 A | 8/1998 | Danielsson et al. | |
| 6,007,532 A | 12/1999 | Netherly | |
| 6,270,466 B1* | 8/2001 | Weinstein | A61B 5/0488 600/590 |
| 6,487,449 B1 | 11/2002 | Kaiser et al. | |
| 6,625,487 B2 | 9/2003 | Herleikson | |
| 6,839,587 B2 | 1/2005 | Yonce | |
| 7,161,362 B2 | 1/2007 | Shambroom et al. | |
| 7,818,058 B2 | 10/2010 | Mentelos | |
| 8,068,905 B2 | 11/2011 | Freeman et al. | |
| 8,089,283 B2 | 1/2012 | Kaplan et al. | |
| 8,412,317 B2 | 4/2013 | Mazar | |
| 2006/0184059 A1* | 8/2006 | Jadidi | A61B 5/04015 600/546 |
| 2007/0018809 A1 | 1/2007 | Reiter et al. | |
| 2008/0004904 A1* | 1/2008 | Tran | A61B 5/0006 705/2 |
| 2008/0027338 A1* | 1/2008 | Lu | A61B 5/0424 600/509 |
| 2008/0275316 A1 | 11/2008 | Fink et al. | |
| 2009/0264792 A1* | 10/2009 | Mazar | A61B 5/0531 600/547 |
| 2010/0100003 A1 | 4/2010 | Chetham et al. | |
| 2011/0105941 A1* | 5/2011 | Jadidi | A61B 5/0488 600/546 |
| 2011/0130675 A1 | 6/2011 | Bibian et al. | |
| 2011/0208028 A1 | 8/2011 | Rossi | |
| 2011/0295096 A1 | 12/2011 | Bibian et al. | |
| 2012/0108999 A1* | 5/2012 | Leininger | A61B 5/0004 600/546 |
| 2013/0012830 A1 | 1/2013 | Leininger et al. | |
| 2013/0030320 A1* | 1/2013 | Maier | A61B 5/0531 600/547 |

OTHER PUBLICATIONS

Davis, Charles S. Statistical methods for the analysis of repeated measurements. Springer Science & Business Media, 2002.*
International Search Report and Written Opinion issued in PCT/US2014/061783 dated Jan. 14, 2015 (18 pages).
Patent Examination Report issued in Australian Patent Application No. 2014340147 dated Aug. 29, 2016 (3 pages).
Extended European Search Report issued in European Patent Application No. 14855373.8 dated Feb. 20, 2017 (7 pages).
English translation of Office Action issued in Japanese Patent Application No. 2016-524597 dated Apr. 25, 2017 (4 pages).
Google Patents English translation of JP2010538775A downloaded on Aug. 7, 2017 (16 pages).

* cited by examiner

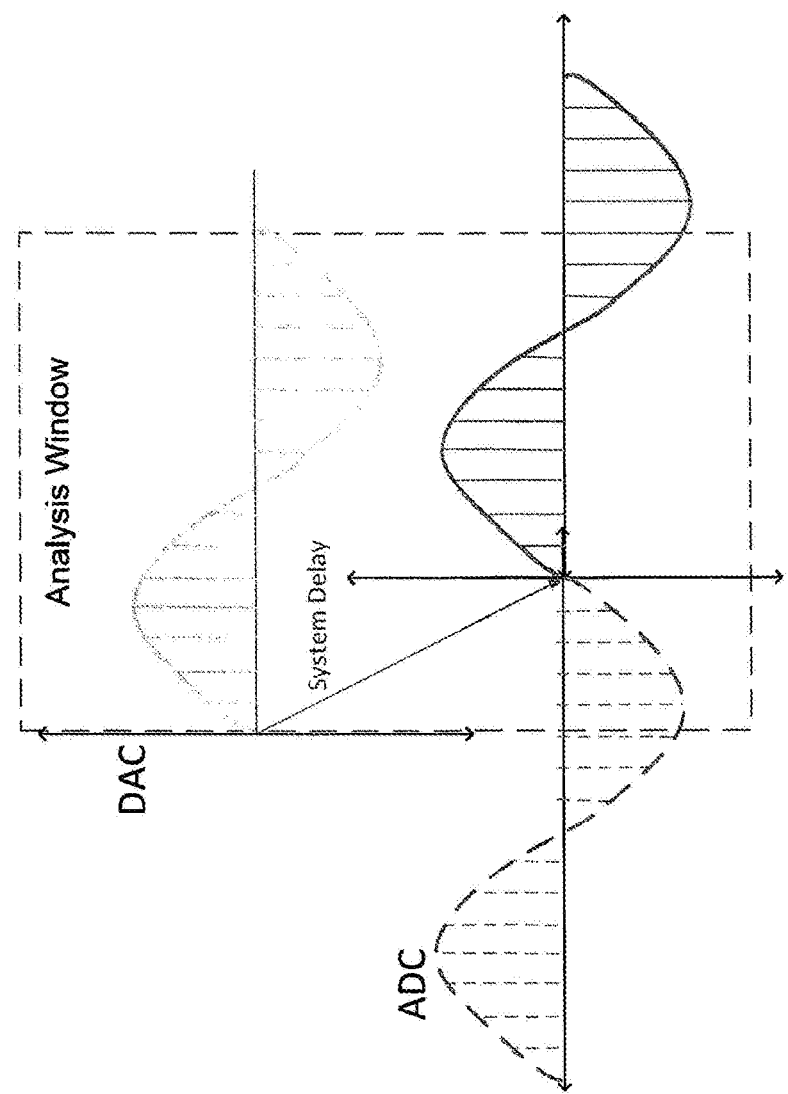

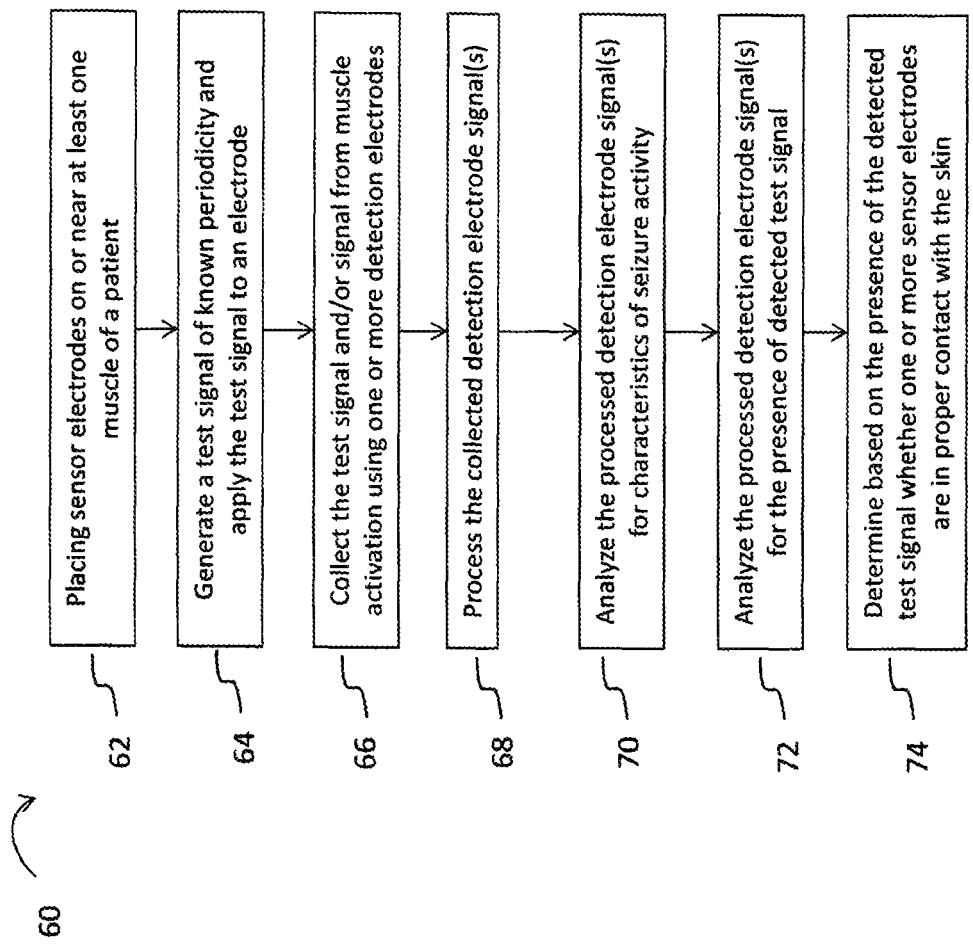

METHOD AND APPARATUS FOR DETECTING SEIZURES INCLUDING LOOSE ELECTRODE MONITORING

CROSS REFERENCE TO RELATED APPLICATION(S)

This application claims priority to International Application No. PCT/US2014/061783 filed Oct. 22, 2014, which claims priority to U.S. Provisional Patent Application No. 61/894,793 filed Oct. 23, 2013 the disclosures of which are herein fully incorporated by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles the activation of which may initiate a redistribution of ions within muscle fibers. In electromyography (EMG), an electrode may be placed on or near the skin and configured to measure changes in electrical potential resulting from ion flow during this muscle activation.

EMG detection may be particularly amenable for use in apparatuses that may be minimally intrusive, minimally interfere with daily activities and which may be comfortably used while sleeping. Therefore, methods of monitoring the seizure activity of patients, including methods for monitoring in ambulatory or home settings, may benefit from the use of EMG detection. To measure electrical signals during EMG, electrodes may be placed on the skin. However, when an electrode becomes loose or loses contact integrity with the skin, it can couple unpredictable noise into the system. A system capable of automatic detection of the skin electrode interface may be used to notify a patient or health care provider of such an event, and may be integrated into a system for patient monitoring.

SUMMARY

In some embodiments, methods of monitoring a patient for seizure activity and for monitoring the contact integrity of electrodes included among an EMG sensor may include generating a test signal of known periodicity and applying the signal to at least one electrode in the sensor system. For example, sensor electrodes may include a common or reference electrode and a pair of detection electrodes, and the test signal may be applied to the common electrode of the sensor. The sensor electrodes may further be attached and positioned such that when properly in contact with the skin the applied test signal may be present at the detection electrodes and collected therein for detection along with electrical activity associated with muscle activation.

In some embodiments, both the applied test signal and any signal collected from muscle electrical activation may be monitored following amplification using a common signal path. For example, both the applied test signal and electrical activity from muscle activation may be processed using at least one shared amplifier. In some embodiments, the test signal may be monitored along one or more paths that are distinct from circuitry configured for collection of muscle activity. In some embodiments, generation or conditioning of an applied test signal may involve setting the applied test signal frequency based upon a clock or oscillator, and in some embodiments, the period of the applied test signal may also be used to establish an analysis window that is used to facilitate detection of the test signal. For example, the period of the applied test signal may be used to define the analysis window, and to distinguish other signal components from the test signal, data may be analyzed for the presence of repetitive characteristics that match the periodicity of the test signal.

BRIEF DESCRIPTION OF THE DRAWINGS

FIG. 3 illustrates a time-varying test signal and the system delay between generation of the test signal and sensing of the test signal.

FIG. 4 illustrates a method of detection seizure activity and monitoring sensor electrodes for contact integrity.

DETAILED DESCRIPTION

Figure 1:
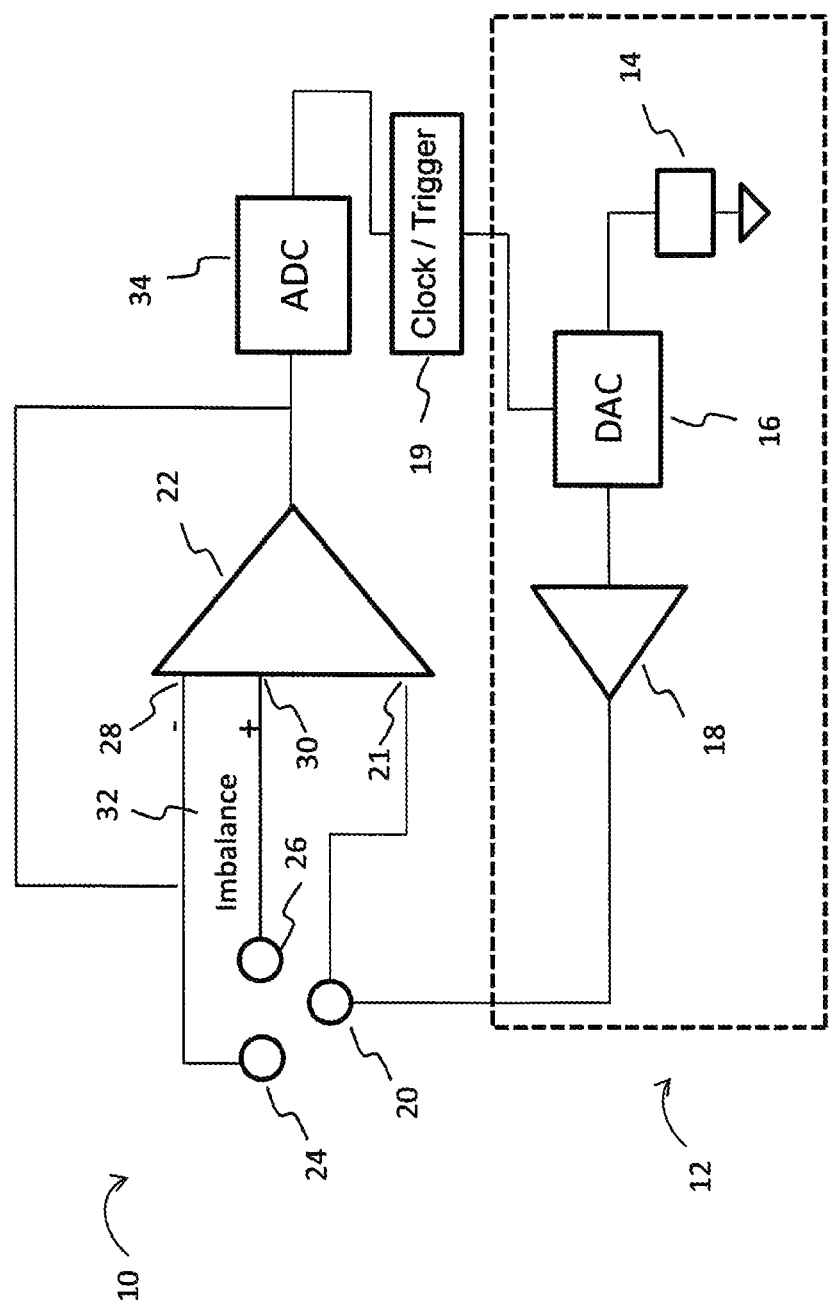
FIG. 1 illustrates one embodiment of a detection system that includes loose electrode monitoring capability.

The following terms as used herein should be understood to have the indicated meanings.

When an item is introduced by "a" or "an," it should be understood to mean one or more of that item.

The term "comprises" means includes but is not limited to.

The term "comprising" means including but not limited to.

The term "detection amplifier" means an amplifier or combination of amplifiers positioned along a circuit pathway configured for collection and processing of electrical signals used to monitor a patient for muscle activity and the presence of seizure activity.

The term "detection electrode" means an electrode positioned along a circuit pathway configured for collection and processing of electrical signals used to monitor a patient for muscle activity and the presence of seizure activity.

The term "having" means including but not limited to.

The apparatuses and methods described herein may be used to detect seizures and timely alert caregivers of seizure-related events using one or more sensors. Sensors may include electrodes attached to a patient or patient's clothing and may be configured for measurement of muscle electrical activity using electromyography (EMG). Detection of seizures using EMG electrodes is further described in Applicant's U.S. patent application Ser. Nos. 13/275,309 and 13/542,596, the disclosures of each of which are herein fully incorporated by reference. As described herein, a test signal may be applied to at least one electrode included among a group of sensor electrodes, and detection of the test signal may be used to monitor the sensor's state. The test signal may, for example, be applied to a sensor's reference electrode and collected for detection at one or more other sensor electrodes. The collected signal may be processed to detect changes in the integrity of an electrode skin interface. When an electrode becomes loose or loses contact integrity with the skin, a fault or warning condition may be indicated.

In some embodiments, a sensor may include a pair of detection electrodes and a reference or common electrode and may be configured to execute bipolar detection of collected signal. The detection electrodes may be placed near a muscle of interest, and signal collected by the detection electrodes may be connected to a detection circuit and analyzed for seizure activity. For example, a signal originating from muscle activity may be collected and sensed following differential signal amplification and analog-to-digital signal processing. A time-varying test signal may further be applied to the system's common electrode, and the applied test signal may be sensed along with any electrical activity associated with muscle activation. In some embodiments, both the applied test signal and any signal collected from muscle electrical activation may be monitored following amplification using a shared signal path. For example, the applied test signal and electrical activity from muscle activation may be processed using at least one shared amplifier. In other embodiments, a test signal may also be injected into the common electrode of a set of bipolar electrodes, but the test signal may be monitored along one or more paths that are distinct from circuitry configured for collection of electrical activity associated with muscle activation. For example, the detection electrodes may be connected to the inverting and noninverting inputs of a differential detection amplifier, and electrical signal from muscle activation detected following amplification using the detection amplifier; however, a test signal collected from one or more of the detection electrodes may be monitored using a circuit path that does not include the detection amplifier.

One embodiment of a seizure detection system that includes loose electrode monitoring capability is shown in FIG. 1. In the detection system 10, a test signal may be injected into a common electrode 20 and sensed along with muscle activity using a shared detection amplifier. The detection system 10 may include circuit components 12 suitable for production of the test signal. For example, a sinusoidal test signal may be generated using a direct current voltage source 14 (e.g., a stable voltage source or suitably referenced battery) and digital-to-analog converter 16. At discrete time intervals, an adjustable portion of the output voltage of source 14 may be selectively passed by digital-to-analog converter 16. Therefore, the output of the voltage source 14 may be segmented to derive a desired profile for the test signal. Amplifier 18 may further be used to condition or adjust the magnitude of the test signal. For example, in some embodiments, the gain of amplifier 18 may be adjusted to control the strength of the applied test signal or amplitude of detected test signal. The test signal may be applied to the reference or common electrode 20 of the sensor, and when the sensor electrodes are suitably in contact with a patient's skin a portion of the test signal may be present and collected at the detection electrodes 24, 26. Signal collected at the detection electrodes 24, 26 may be directed to the inputs 28, 30 of a detection amplifier 22, and the output of the amplifier 22 processed for signal detection. For example, amplifier 22 may be connected to an analog-to-digital converter 34 for digital processing and then fed into a microprocessor (not shown) for analysis and/or visualization. Clock or trigger element 19 may be connected to either of analog-to-digital converter 34 or an associated microprocessor connected therein. Clock element 19 may also be used in generation of the test signal. For example, as shown in FIG. 1, clock element 19 may be linked to digital-to-analog converter 16, and intervals of time for segmentation of the voltage source 14 may be set or triggered using the clock element 19. Therefore, as further described below, the test signal and circuitry used for analysis of detected signal may, in some embodiments, operate in a synchronized manner.

Synchronization of test signal generation and detection may, in some embodiments, include partitioning collected signal into periods of analysis that are a known multiple of the test signal period. Because an analysis period may be set to be a time duration that may be a known and/or constant number of test signal periods a constant or expected number of any repetitive characteristics of the test signal may be expected during any given analysis window. Other signal components may generally not be synchronized with the analysis window. Therefore, other signal components may only maintain a random or non-constant relationship with various analysis windows. Discrimination between test signal and other signal components may therefore be enhanced by looking for repetitive signal characteristics that maintain the expected periodicity of the applied test signal. While the test signal may conveniently follow a sinusoidal variation of amplitude within a given period, other periodically varying test signal profiles may, in some embodiments, also be used. By way of nonlimiting example, the test signal may be characterized as having an amplitude that varies based on a sinusoidal, saw-tooth, triangular, square, or other periodic form or shape. The aforementioned shapes may, in some embodiments, be generated using a combination of direct current voltage source 14 and digital-to-analog converter 16. For example, the digital-to-analog converter 16 may function as a time varying filter, selectively adjusting voltage passed to segment the constant amplitude output of source 14, the amplitude of individual segments being selected, for example, using an appropriate look-up table. In some embodiments, the test signal may be a 3 KHz sine wave produced in segments of varying amplitude using a 16 or 32 point look-up table. However, as understood by those of ordinary skill in the art, other suitable methods of producing a time varying signal may also be used.

In some embodiments, the test signal may be a time-varying signal with a frequency that is outside of a frequency range analyzed for seizure detection with EMG. For example, the test signal may include a waveform with a repetition frequency of about 1 KHz to about 5 KHz or about 2.8 KHz to about 3.2 KHz, and signal analyzed for seizure activity may include frequency data in a range between about 20 Hz to about 500 Hz. In some embodiments, signal analyzed for seizure activity may include frequency data in a range between about 30 Hz to about 240 Hz, and the test signal may be a waveform with a repetition frequency of about 1 KHz to about 5 KHz or about 2.8 KHz to about 3.2 KHz.

The test signal may be applied to the reference or common electrode 20 which, as shown in FIG. 1, may be connected to a reference input 21 of the detection amplifier 22. Electrode 20 may further be configured for attachment on a patient's skin. Also configured for attachment on the patient's skin, the detection system 10 may include the pair of detection electrodes 24, 26. The detection electrodes 24, 26 may be connected to the inverting and noninverting inputs 28, 30 of the detection amplifier 22, and any difference in electrical potential or voltage between the inputs 28, 30 may be amplified to encourage high sensitivity detection of localized electrical signal from muscle activity originating near the electrodes 24, 26. The test signal or a portion of the test signal may further be present at the electrodes 24, 26 in intensity depending, for example, on the test signal amplitude, relative positioning of the electrodes 20, 24, 26, relative impedance of skin and other tissues located between the set of electrodes (20, 24, and 26), and the input impedance of the electrodes 20, 24, and 26. In some embodiments, the collection of electrodes 20, 24, 26 may be provided separately or provided together in a mounting unit. For example, a mounting unit may include slots wherein the individual electrodes may be inserted and/or reproducibly positioned together in an integrated assembly.

In some embodiments, the intensity of the applied test signal and positioning of electrodes may be adjusted such that at least a portion of the applied test signal is present at one or more detection electrodes. For example, in some embodiments, a test signal of about 1 mV to about 750 mV may be applied to a common electrode generally located about 0.5 cm to about 3 cm from a pair of detection electrodes. The test signal may be large enough to create a sine wave of low harmonic distortion, and, in some embodiments, the test signal may be suitable in intensity and low enough in harmonic distortion to minimize the presence of harmonic signal from the test signal within bandwidth regions used for EMG detection.

In some embodiments, the detection electrodes 24, 26 may be connected to a differential detection amplifier, and any signal that is common between the electrodes, such as may be typical of environmental or noise components generated at a distance from the detection region and unrelated to signal from muscle activation intended for detection, may be rejected. For example, as understood in the art, the detection amplifier 22 may be a differential amplifier and may be characterized as having a capability for common-mode rejection of signal components that may be present at each of the detection electrodes 24, 26. Test signal that may be present in equivalent amplitude at each of the detection electrodes 24, 26 and may, therefore, tend to be detected with low sensitivity. However, in some embodiments, the system 10 may be configured to maintain an imbalance potential 32 between the inputs 28, 30 of detection amplifier 22 when the system is properly connected (and the sensor electrodes maintain suitable contact with the skin), and that imbalance potential may be related to the applied test signal. Because the imbalance potential may be related to the test signal, the test signal may therefore be continuously monitored and detected with high sensitivity. For example, in some embodiments, the system 10 may be configured to maintain an imbalance potential 32 of about 0.1 mV to about 10 mV or typically about 0.5 mV to about 2 mV when the electrodes are properly in contact with the skin.

In some embodiments, the relative position of the electrodes and/or relative impedance values of electrodes 24, 26 may be adjusted to encourage the presence of imbalance potential or voltage 32. For example, decreasing the relative impedance for one of the electrodes 24 or 26 may decrease the magnitude of potential drop for any signal collected at the electrode of reduced impedance, and the potential output from the electrode (or potential at the amplifier input connected to the electrode of reduced impedance) may therefore be raised. When each of the electrodes (20, 24, and 26) maintains contact integrity with the skin, the electrode contacts and adjoining skin between the electrodes may connect the test signal from the common electrode 20 to each of the detection electrodes 24, 26, but the potential at the outputs of the detection electrodes 24, 26 may be slightly different because of the aforementioned impedance imbalance. Therefore, in some embodiments, an imbalance potential or voltage 32 may be encouraged because the test signal may experience a different potential drop across the two detection electrodes 24, 26.

In some embodiments, electrodes 24, 26 may have input resistance values (or similar impedance at about 3 KHz) of about 2 KΩ to about 20 KΩ, but one of the electrodes 24, 26 may include an input resistance that is about 1% to about 10% lower in magnitude than the other electrode. In some embodiments, one or more of the detection electrodes may include or be connected to a resistive element suitable to adjust a potential drop across the electrode or electrode/element combination and therefore modify or set the imbalance potential 32. For example, each of the electrodes 24, 26 may have input resistance values of about 2 KΩ to about 20 KΩ, but one of the electrodes may be connected in series to a resistor that is about 1% to about 10% of the resistance value of the electrodes 24, 26. For example, the electrodes may have an input resistance of about 2 KΩ, but one of the electrodes may be connected in series to a resistor that is about 20Ω to about 200Ω of the resistance value of the electrodes. By way of further example, the electrodes may have an input resistance of about 20Ω, but one of the electrodes may be connected in series to a resistor that is about 200Ω to about 2 KΩ of the resistance value of the electrodes. In some embodiments, at least one of the detection electrodes 24, 26 may be connected to an element in a manner to suitable to change a voltage drop across the electrode and/or combination of the connected element and electrode.

In some embodiments, a circuit element may be included in at least one of the detection electrodes 24, 26 or added along a circuit path leading to at least one of the amplifier inputs 28, 30 wherein the element may have an impedance value that may be greater at high frequency values but lower at lesser frequency values. Therefore, in some (but not all embodiments), the imbalance potential may be frequency dependent. For example, one of the detection electrodes or an added circuit element may have one impedance at the frequency of the test signal, but the impedance may be less for signals that are lower in frequency than the test signal frequency. In some embodiments, either or both of the circuit paths leading between the detection electrodes 24, 26 and the amplifiers inputs 28, 30 may include a capacitive element or combination of one or more resistors, capacitors, and/or inductors to adjust the impedance and/or to make the impedance frequency dependent. For example, one or more of the aforementioned elements may be configured as a suitable filter. In some embodiments, a low pass filter may be added between one of the detection electrodes 24, 26 and the amplifiers inputs 28, 30, and the imbalance 32 may be frequency dependent. For example, an imbalance 32 may be maintained at a first potential (e.g., maintain an about 0.1 mV to about 10 mV potential) for frequencies above about 1 KHz when the system 10 is properly connected, but low frequency components of the imbalance (e.g., at frequencies less than about 500 Hz) may only be present at much lower values (e.g., less than about 50 microvolts).

In some embodiments, the imbalance may be actively or passively controlled to range between about 0.1 mV to about 10 mV or typically about 0.5 mV to about 2 mV. Within those ranges, a suitable imbalance potential may be present in order to encourage high sensitivity detection of test signal. While the test signal may generally be more detectable for higher values of the imbalance potential 32, imbalance potentials 32 that are too high may generally impact the common-mode-rejection ratio of the amplifier 22. For example, with too high of an imbalance potential, unwanted sources of noise may inadvertently be coupled into the amplifier 22 and the background signal upon which muscle related signals are discriminated may be higher than desired for high sensitivity detection. In the system 10, the EMG detection circuitry is also directed through the amplifier 22, and generally a high common-mode rejection may be desired to improve system sensitivity. Therefore, an imbalance potential 32 of about 0.1 mV to about 10 mV may be a compromise value wherein, surprisingly, both signal from muscle activation and test signal are present in the detection circuitry at levels above system noise, and each may be detected using appropriate circuitry. Moreover, the system 10 may be configured for continuous detection of both the test signal and electrical signal from muscle activation. For example, the system 10 may actively monitor both a test signal and signal from muscle activation without periodically switching the system between a state suitable for monitoring the test signal and a state suitable for monitoring electrical signals derived from muscle activation. Furthermore, for monitoring a patient in an ambulatory setting, minimizing battery requirements may be beneficial. In the system 10, a shared amplifier 22 for amplification of both test signal and signal from muscle activity is used, and the need for multiple amplifiers and/or signal paths (and concomitant energy use or dissipation with associated additional circuit elements) may be lessened.

As described above, the value of the potential imbalance 32 may generally affect the common-mode-rejection ratio of the detection amplifier 22 and overall system noise, and in some embodiments, the system 10 may be configured to operate with a finite imbalance 32 when the system is properly connected to the skin. In some embodiments, the system 10 may be configured to monitor the imbalance potential 32 by directly measuring the potential during system calibration. In some embodiments, the system 10 may be configured to monitor the strength of a detected test signal during calibration. For example, one or more elements of the system 10 may be adjustable, and in some embodiments, adjustment may be used to calibrate the system and maintain a finite imbalance potential 32 or detectable test signal when the system is properly connected to the patient. For example, the imbalance during calibration may be controlled to have a value of about 0.1 mV to about 10 mV or about 0.5 mV to about 2 mV. By way of nonlimiting example, the intensity of the generated or applied test signal and or impedance of one or more electrodes or elements connected to the electrodes may be adjusted to set the imbalance 32 during calibration. For example, any of the aforementioned resistors or resistive elements that may be connected to a detection electrode may be, e.g., variable resistors. In some embodiments, the imbalance 32 may be measured directly when electrodes are attached to a patient's skin, and if the imbalance 32 is not within an expected range, the system may be deemed out of calibration. In some embodiments, the imbalance 32 may be set or adjusted to a level suitable to maintain a detectable level of the test signal above a noise level. For example, if suitable sensitivity of detection is only achieved with an imbalance exceeding a predetermined threshold, the system may send out a warning that the system is not within specifications. In some embodiments, the imbalance 32 may be set or adjusted to a level suitable to detect the test signal and also set or adjusted to maintain a minimum common-mode rejection for the detection amplifier 22. For example, if suitable sensitivity for detection of a test signal is achieved during calibration but a threshold common-mode rejection ratio is not met a warning may be indicated that the system is not calibrated and/or improperly connected. In some embodiments, the intensity of the detected test signal may be monitored during calibration, and in some embodiments, if the intensity of the detected test signal is low the intensity of the applied test signal may be increased. For example, the applied test signal may, in some embodiments, be increased by adjusting the gain of amplifier 18, magnitude of voltage source 14, value of a look-up-table, or combinations thereof.

In the system 10, each of the test signal and EMG signal are connected to detection amplifier 22 for processing, and the output of detection amplifier 22 may include signal derived from both signals. Further, as shown in FIG. 1, amplifier 22 may be connected to an analog-to-digital converter 34. The digital output provided from analog-to-digital converter 34 may be fed into a microprocessor (not shown) for analysis and/or visualization. Clock or oscillator element 19 may be connected to either of analog-to-digital converter 34 or an associated microprocessor connected therein and used to synchronize generation and analysis of sensed signal as further described below.

In some embodiments, a bandpass or high pass filter (not shown) may be added in the circuit path between the detection amplifier 22 and analog-to-digital converter 34, and the filter may be selected in order to improve sensitivity for sensing the test signal. For example, an injected test signal may have a frequency of about 1 KHz to about 5 KHz or about 2 KHz to about 4 KHz, and in some embodiments, a suitable bandpass filter may be added to isolate the test signal frequency from other frequency components including those associated with muscle activity. In some embodiments, the detection system 10 may be configured to sense a 3 KHz test signal and also to sense one or more frequency bands between about 20 Hz to about 500 Hz. Data sensed within frequencies between about 20 Hz to about 500 Hz may, for example, be used to calculate one or more values related to muscle activation and which may correlate with seizure activity. In some embodiments, determining whether collected signal corresponds with seizure activity may include determining whether the collected signal meets a threshold value of a characteristic related to muscle electrical activity. For example, in some embodiments, a threshold value may be associated with one of a T-squared statistical value, detection of a plurality of EMG data bursts, detection of a characteristic GTC waveform, or combinations thereof.

Figure 2:
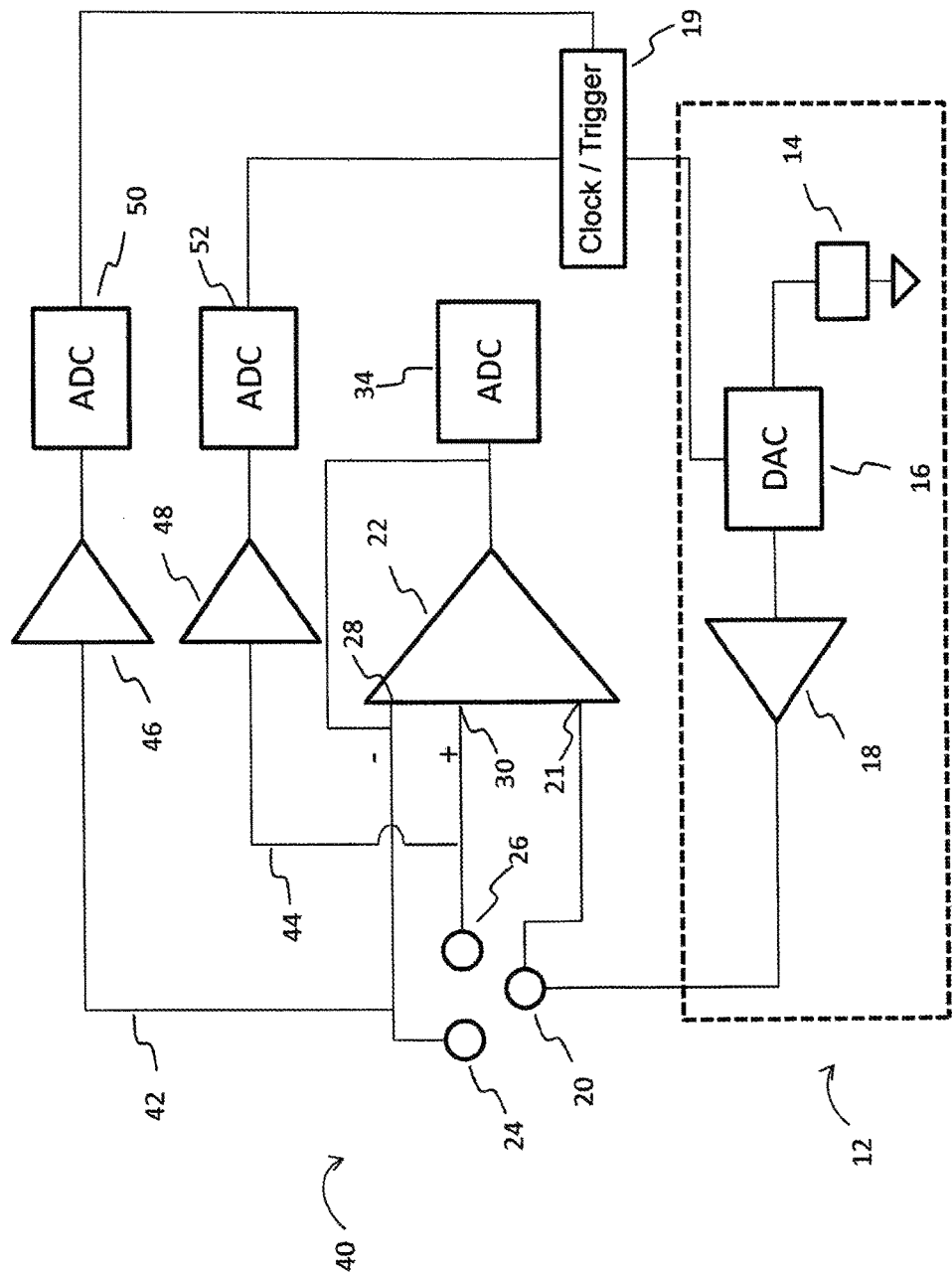
FIG. 2 illustrates another embodiment of a detection system that includes loose electrode monitoring capability.

In FIG. 1 both the test signal and electrical activity originating from muscle are conveniently monitored using common circuitry, and in some embodiments, the signals may be monitored using a single detection amplifier. FIG. 2 illustrates another embodiment of a detection system 40, which also includes the capability to monitor electrode contact integrity, and includes discrete circuit paths for detection of test signal and muscle activity. For clarity elements that may be similar or serve related functions in some embodiments of the detection systems 10 and 40 are marked with the same reference numbers. In the detection system 40, a test signal may be produced and/or conditioned along circuit path 12, and like the system 10, the test signal may be a time varying signal. The detection electrodes 24, 26 may be connected to detection amplifier 22 and collected signal from the electrodes or differential signal between the electrodes may be amplified. However, unlike the embodiment of detection system 10, in the system 40, either or both of the detection electrodes 24, 26 may also be connected to the respective circuit paths 42, 44. Each of the signal paths 42, 44 may include processing elements appropriate for monitoring the presence of an applied test signal. Because signal derived from muscle activity may be directed and monitored using circuitry associated with the amplifier 22, high efficiency frequency dependent circuit elements, such as high-rejection ratio bandpass or high pass filters, that may be highly selective for passing a test signal frequency may be included at any point along signal paths 42, 44 without risking degradation of signal within frequencies useful for the monitoring of seizure characteristics.

In some embodiments, the signal paths 42, 44 may include amplifiers 46, 48 and analog-to-digital converters 50, 52. Amplifiers 46, 48 may be differential amplifiers, but may also be simpler and/or energy efficient summing amplifiers. In some embodiments, bandpass or high-pass filters may be included or other elements appropriate to enhance detection of the test signal may be added. The digital output provided from analog-to-digital converters 50, 52 may be fed into one or more microprocessors (not shown) for analysis. Further in the system 40, output from the detection amplifier 22 may be processed by analog-to-digital converter 34. In some embodiments, a low-pass filter may be added, for example between amplifier 22 and analog-to-digital converter 34 to enhance sensitivity for detection of signal from muscle activation. Any one of the analog-to-digital converters (34, 50, and 52) or associated microprocessor may be triggered as further described herein using the clock or oscillator element 19.

As described above, each of the detection systems 10, 40 may be configured to generate a test signal (e.g., using circuit path 12), inject the test signal at one electrode, and detect the test signal following collection and processing. For example, detection of the applied test signal may include analysis of a signal that may be fed into one or more microprocessors. A signal may be analyzed by collecting or partitioning signal over a series of discrete analysis time windows, and in some embodiments, the analysis time window may be correlated with the temporal variation of the generated test signal. For example, the sensed signal may be broken up into time windows of duration that are a known number of multiples of the generated test signal period. Thus, in some embodiments, a time window used for analysis of a sensed signal may be related to a period of time in which the applied test signal oscillates. In further embodiments, a time window for analysis of a sensed signal may be related in duration to the period of the applied test signal, and the phase between the time window and applied test signal may be held constant.

Correlation of the period of an applied test signal and a window of time for analysis of sensed signal may, by way of nonlimiting example, be accomplished by synchronizing operation of at least one of the analog-to-digital converters (34, 50, or 52) or an integration circuit of an associated microprocessor and one or more elements used to create or fashion the test signal (e.g., elements associated with circuit path 12). For example, at least one element used on the analysis side of the circuit and one element used to generate the test signal may be synchronized. In some embodiments, correlation of the analysis windows and test signal generation may be achieved by triggering the analysis window and one element used to generate the test signal (e.g., digital-to-analog converter 16) using a common clock or oscillator element. For example, the triggering of a start time for integration and/or for execution of a frequency transform of the sensed signal and one element used to generate the test signal may be set or based upon the same clock signal. For example, in some embodiments, sampling of data from one of the analog-to-digital converters (34, 50, and/or 52) may be triggered in a synchronous manner with segmentation of the test pulse during its generation. For example, for each time (or for each of an integral number of times) that digital-to-analog converter 16 uses a value on a look-up-table to segment the test signal, an analog-to-digital converter (34, 50, and/or 52) may send data to a microprocessor for analysis. Therefore, within a given analysis window, sensed data may also be segmented (on the detection side) in a synchronized manner to the test pulse. Moreover, because a rate of data segmentation may be known on both the detection side for sensed signal and on the generation side for the test pulse an analysis window may be defined to include a number of segments that matches a period (or integral number of periods) of the generated test signal. Moreover, in this approach, any phase delay that may occur during processing of the test pulse, e.g., between segmentation of the test signal and sampling of data used in an analysis window may remain constant. Therefore, the timing and length of the analysis window (or discrete data values within the analysis window) and test signal period may maintain a constant phase relationship and may be reproducibly synchronized.

Because the analysis window may repeatedly include one or some integral number of peaks of maximum amplitude and/or minimum amplitude if the test pulse is sensed on the detection side of the circuitry (and because sensing of the test pulse may be dependent on proper electrode contact), peak-to-peak variation of the sensed signal may be minimized when contact integrity of the electrodes is maintained. For example, synchronization of generation and sampling, as described above, may prevent random variation of an unknown number of peak maximum and/or minimum values. Therefore, in some embodiments, even with only a single period of test signal sampled (i.e., with a sample window that is one period of the test signal) the test pulse may be reliably detected.

For example, in FIG. 3, a time varying test signal output from digital-to-analog converter 16 is schematically shown together with a window for analysis of signal, such as may be output from one of the analog-to-digital converters 34, 50, 52. As shown in FIG. 3, because both the sample window and generation of test signal are triggered from a common oscillator the phase delay may be known or constant and a reliable and integral number of maximum and/or minimum value peaks may be detected in any analysis window. To distinguish other signal components from the test signal, data may be analyzed for the presence of repetitive characteristics that match the periodicity of the test signal. For example, in some embodiments, data for a collected time window may indicate the test signal if the number of positive and/or negative amplitude peaks matches an expected value, if the amplitude is suitably high or if a system delay is reproducibility detected in one or more analysis windows. In some embodiments, data for a collected time window may indicated sensing the test signal if the number of positive and/or negative amplitude peaks matches an expected value and the peaks or a rectified value of the total signal reaches a threshold level.

A method 60 of monitoring a sensor system for seizure activity using electromyography and for checking the skin contact integrity of at least one electrode included in the sensor is shown in FIG. 4. In a step 62, sensor electrodes may be placed on or near at least one muscle of a patient for which electrical activity may be monitored and related to seizure characteristics. For example, in preferred embodiments, a pair of detection electrodes may be placed on a muscle of interest (such as the biceps or triceps), and a common or reference electrode placed an appropriate distance from the pair of detection electrodes. The common electrode may, for example, be placed near a region of electrically unrelated tissue or region of tissue that may be relatively free of the electrical signal of interest.

In a step 64, a test signal of known periodicity may be generated and/or applied to an electrode included among the sensor system. For example, the test signal may be applied to the common electrode of sensor electrodes arranged in a bipolar detection configuration. In some embodiments, the test signal may have a frequency of about 1 KHz to about 5 KHz signal, 2 KHz to about 4 KHz, or about 3 KHz. Test signal data may, for example, be generated in a series of segments with a periodicity established using a clock or oscillator. The intensity of the applied test signal and positioning of electrodes may be adjusted such that at least a portion of the applied test signal is present at one or more detection electrode. For example, in some embodiments, a test signal of about 1 mV to about 750 mV may be applied to a common electrode generally located about 0.5 cm to about 3 cm from a pair of detection electrodes.

In a step 66, signal may be collected at one or more detection electrodes. For example, the signal may include a portion of the test signal and signal (if present) from muscle activation. In some embodiments, collection of signal may be achieved using a pair of detection electrodes wherein the input impedance of the detection electrodes is about 2 K$\Omega$ to about 20 K$\Omega$. In some embodiments, the input impedance of the detection electrodes may be equivalent and application of about the same input voltage at the electrodes may yield an output signal that is balanced. In other embodiments, the input impedance of the detection electrodes may be unbalanced and for about the same applied voltage to the detection electrodes an imbalance potential may be present.

In a step 68, a collected detection electrode signal (EMG signal) may be processed. For example, signal collected from a detection electrode may include an EMG signal and the applied test signal. In some embodiments, processing collected detector electrode signal may include, by way of nonlimiting example, directing the signal through one or more amplifiers, application of one or more filters (such as may be used to isolate either test signal data or signal resulting from muscle activation), segmentation of sensed signal data, digitizing analog data, other processing, and any combinations thereof.

In a step 70, the collected signal may be analyzed for characteristics of seizure activity. For example, in some embodiments, the collected signal may be analyzed for the presence of one or more characteristics or threshold values related to seizure activity including by way of nonlimiting example a threshold T-squared statistical value, presence of amplitude bursts, detection of a characteristic GTC waveform, or combinations thereof.

In a step 72, the collected signal may be analyzed for the presence of detected test signal. In some embodiments, the signal analyzed for the presence of test signal may be segmented in a manner that is correlated to segmentation during generation of the test signal. For example, analyzed signal and the generated test signal may be synchronized in duration and/or phase.

In a step 74, based on the presence of the detected test signal, a determination may be made whether the one or more sensor electrodes are in proper contact with the skin and appropriate actions may be elicited. For example, if it is determined that the test signal is not detected or does not meet a threshold level a warning may be indicated.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. Use of the word "include," for example, should be interpreted as the word "comprising" would be, i.e., as open-ended. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

What is claimed is:

1. A method of monitoring a patient for seizure activity by collecting data with an electromyography sensor and for checking the contact integrity of electrodes included in the sensor, the method comprising:
    positioning a pair of detection electrodes and a common electrode on the skin of a patient on or near at least one muscle in order to provide a group of positioned electrodes, said pair of detection electrodes being connected to inputs of a differential amplifier, said electromyography sensor being configured to maintain an imbalance potential at said inputs of said differential amplifier when said contact integrity is maintained between the skin and said group of positioned electrodes, wherein the imbalance potential enhances amplification of a test signal collected by said pair of detection electrodes;
    applying said test signal to said common electrode;
    collecting a signal from said pair of detection electrodes;
    analyzing said collected signal for characteristics of seizure activity;
    analyzing said collected signal for detection of said test signal; and
    determining based on the detection of said test signal whether said contact integrity is maintained between the skin and said group of positioned electrodes.

2. The method of claim 1 wherein said determination of whether said contact integrity is maintained between the skin and said group of positioned electrodes includes establishing whether a threshold amplitude level of said test signal is met.

3. The method of claim 1 wherein said group of positioned electrodes are configured such that when said contact integrity between the skin and said group of positioned electrodes declines, an amplitude of said detected test signal decreases.

4. The method of claim 1 wherein said electromyography sensor is portable and configured for use in an ambulatory or home setting.

5. The method of claim 1 wherein at least one of the detection electrodes in said pair of detection electrodes is connected to at least one input in said inputs of said differential amplifier in series through a resistive element.

6. The method of claim 5 wherein said resistive element is an about 20$\Omega$ to an about 200$\Omega$ resistor.

7. The method of claim 1 wherein said imbalance potential is established through a low pass filter connected to at least one of the detection electrodes in said pair of detection electrodes.

8. The method of claim 1
    said pair of detection electrodes having different impedance values, the impedance value difference being suitable to maintain said imbalance potential between the inputs of said differential amplifier when said contact integrity is maintained between the patient's skin and said group of positioned electrodes.

9. The method of claim 8, a first detection electrode in said pair of detection electrodes having an input impedance of about 2 K$\Omega$ to about 20 K$\Omega$; and the second detection electrode in said pair detection electrodes having an input impedance magnitude of about 1% to about 10% lower than the input magnitude of the first detection electrode.

10. The method of claim 8, wherein at least one of the impedance values for the detection electrodes in said pair of detection electrodes being greater for applied frequencies above about 1 KHz than for applied frequencies within a range of about 20 Hz to about 500 Hz.

11. The method of claim 1
said positioning of electrodes being sufficient to create said imbalance potential when said contact integrity is maintained between the skin and said group of positioned electrodes.

12. The method of claim 1
at least one of said pair of detection electrodes being connected to an electrical component having sufficient impedance to create said imbalance potential when said contact integrity is maintained between the skin and said group of positioned electrodes.

13. The method of claim 12 wherein said electrical component is an about 20Ω to an about 200Ω resistor.

14. The method of claim 1, the test signal being a time-varying test signal within the frequency range of about 1 KHz to about 5 KHz; and
said analyzing said collected signal for seizure activity including evaluating the collected signal for muscle electrical activity in a frequency range between about 20 Hz to about 500 Hz.

15. The method of claim 1, said analyzing said collected signal for seizure activity includes determining whether said collected signal meets a threshold value of a characteristic related to muscle electrical activity.

16. The method of claim 15 wherein said threshold value is a T-squared statistical value calculated from an EMG power spectrum.

17. The method of claim 15 wherein said threshold value comprises detection of a plurality of EMG data bursts.

18. The method of claim 1 wherein the test signal is a time-varying test signal with a controlled period.

19. The method of claim 18, said analyzing the collected signal for detection of said test signal comprising:
partitioning the collected signal into an analysis window, the analysis window being an integral number of multiples of the test signal period; and
determining whether one or more repetitive characteristics that match the periodicity of the test signal are detected in the analysis window.

20. The method of claim 19, a phase delay between the analysis window and the applied test signal being constant.

21. The method of claim 19, said analysis window being some integral multiple of oscillations of a clock or oscillator; and
the test signal period being controlled using said clock or oscillator.

22. The method of claim 19 wherein said repetitive characteristic is selected from a group of characteristics including phase delay, signal amplitude, number of positive amplitude peaks, and number of negative amplitude peaks.

23. The method of claim 18 wherein said analyzing the collected signal for said detection of said test signal comprises:
partitioning the collected signal into an analysis window; the analysis window being an integral number of multiples of the test signal period;
determining a number of positive and/or negative amplitude peaks; and
determining whether the number of positive and/or negative amplitude peaks matches an expected value.

* * * * *